US010881615B2

(12) United States Patent
He et al.

(10) Patent No.: US 10,881,615 B2
(45) Date of Patent: Jan. 5, 2021

(54) PHARMACEUTICAL COMPOSITION COMPRISING DABIGATRAN ETEXILATE, AND PREPARATION METHOD, SOLID PREPARATION AND USE THEREOF

(71) Applicant: Chia Tai Tianqing Pharmaceutical Group Co., Ltd., Lianyungang (CN)

(72) Inventors: Xiongxiong He, Lianyungang (CN); Ping Dong, Lianyungang (CN); Jiahui Cai, Lianyungang (CN); Xin Huang, Lianyungang (CN); Xiquan Zhang, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 204 days.

(21) Appl. No.: 15/525,860

(22) PCT Filed: Nov. 13, 2015

(86) PCT No.: PCT/CN2015/094499
§ 371 (c)(1),
(2) Date: May 10, 2017

(87) PCT Pub. No.: WO2016/074640
PCT Pub. Date: May 19, 2016

(65) Prior Publication Data
US 2017/0333350 A1 Nov. 23, 2017

(30) Foreign Application Priority Data

Nov. 14, 2014 (CN) .......................... 2014 1 0650786

(51) Int. Cl.
| | | |
|---|---|---|
| *A61K 9/16* | (2006.01) | |
| *A61K 31/4402* | (2006.01) | |
| *A61K 47/30* | (2006.01) | |
| *A61K 47/38* | (2006.01) | |
| *A61K 31/4439* | (2006.01) | |
| *A61K 47/22* | (2006.01) | |
| *A61P 7/02* | (2006.01) | |
| *A61P 9/10* | (2006.01) | |

(52) U.S. Cl.
CPC .......... *A61K 9/1676* (2013.01); *A61K 9/1617* (2013.01); *A61K 9/1623* (2013.01); *A61K 9/1635* (2013.01); *A61K 9/1641* (2013.01); *A61K 9/1652* (2013.01); *A61K 9/1682* (2013.01); *A61K 31/4402* (2013.01); *A61K 31/4439* (2013.01); *A61K 47/30* (2013.01); *A61K 47/38* (2013.01); *A61P 7/02* (2018.01); *A61P 9/10* (2018.01); *A61K 47/22* (2013.01)

(58) Field of Classification Search
CPC .. A61K 9/1676; A61K 9/1635; A61K 9/1623; A61K 9/1641; A61K 9/1617; A61K 9/1652; A61K 9/1682; A61K 31/4402; A61K 47/30; A61K 47/38; A61K 31/4439; A61K 47/22; A61K 9/5078; A61P 9/10; A61P 7/02

See application file for complete search history.

(56) References Cited

U.S. PATENT DOCUMENTS

| | | | |
|---|---|---|---|
| 4,367,217 A | 1/1983 | Gruber | |
| 4,438,091 A | 3/1984 | Gruber | |
| 9,089,488 B2 | 7/2015 | Radtke | |
| 2003/0181488 A1* | 9/2003 | Brauns | C07D 401/12 514/338 |
| 2011/0123635 A1 | 5/2011 | Radtke | |
| 2013/0243856 A1* | 9/2013 | Dharmadhikari | A61K 9/2072 424/465 |
| 2013/0251810 A1 | 9/2013 | Landerer | |

FOREIGN PATENT DOCUMENTS

| | | |
|---|---|---|
| CA | 2476054 A1 | 9/2003 |
| CN | 1638771 A | 7/2005 |
| CN | 101632668 A | 1/2010 |
| CN | 101980697 A | 2/2011 |
| CN | 102099012 A | 6/2011 |
| CN | 103127109 A | 6/2013 |
| CN | 102793699 B | 6/2014 |
| CN | 104042588 A | 9/2014 |
| EP | 1485094 A1 | 12/2004 |
| WO | WO 2003074056 A1 | 9/2003 |
| WO | WO 2011/107749 A2 | 9/2011 |
| WO | WO 2012001156 A2 | 1/2012 |

OTHER PUBLICATIONS

FDA, Guidance for Industry Dissolution Testing of Immediate Release Solid Oral Dosage Forms, pp. 1-11. (Year: 1997).*
Liu, W. et al.; "Evaluation of Curative Effect an Safety of Dabigatran"; Adv. Cardiovasc. Disc., vol. 35, No. 5, pp. 581-586; Sep. 2014, with English translation of abstract; DOI:10.3969/j. issn. 1004-3934. 2014.05.016 (6 pages).
Extended European Search Report in European Patent Application No. 15859607.2, dated Jun. 7, 2018 (11 pages).

* cited by examiner

*Primary Examiner* — Abigail Vanhorn
(74) *Attorney, Agent, or Firm* — Nixon Peabody LLP

(57) ABSTRACT

A pharmaceutical composition comprising dabigatran etexilate, and preparation method and use thereof, and solid preparation comprising the pharmaceutical composition; the pharmaceutical composition comprises a vitamin C layer and a dabigatran etexilate layer separated by a semipermeable film layer, and the semipermeable film layer comprises a water-soluble compound, a water-insoluble compound and an optional anti-sticking agent and/or plasticizer.

14 Claims, 1 Drawing Sheet

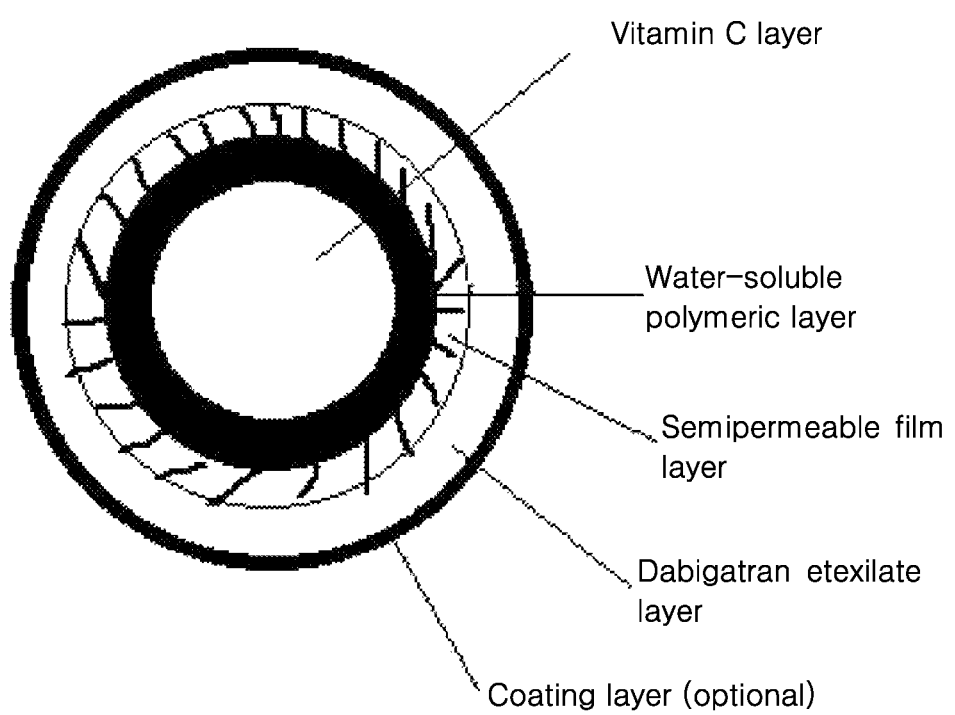

PHARMACEUTICAL COMPOSITION COMPRISING DABIGATRAN ETEXILATE, AND PREPARATION METHOD, SOLID PREPARATION AND USE THEREOF

CROSS-REFERENCE TO RELATED APPLICATIONS

This application is a U.S. national stage of PCT/CN2015/094499, filed on Nov. 13, 2015, which claims priority to Chinese Patent Application No. 201410650786.1 filed on Nov. 14, 2014, the contents of which are each incorporated herein by reference in their entireties.

FIELD OF THE INVENTION

The present invention relates to a pharmaceutical composition comprising dabigatran etexilate, and a preparation method, a solid preparation and a use thereof, and belongs to the field of medicinal technology.

BACKGROUND OF THE INVENTION

The chemical structure of the active substance dabigatran etexilate according to the present invention is 3-[(2-{[4-(hexyloxycarbonylamino-imino-methyl)-phenylamino]-methyl}-1-methyl-1H-benzimidazol-5-yl-carbonyl)-pyridin-2-yl-amino]-ethyl propionate, represented by chemical formula I. This compound can be used for reducing the risk of stroke and systemic embolism in patients with non-valvular atrial fibrillation, treating deep venous thrombosis and pulmonary embolism in patients who have been treated with parenteral anticoagulants for 5-10 days, or reducing the risk of recurrence of deep venous thrombosis and pulmonary embolism in patients who have been treated.

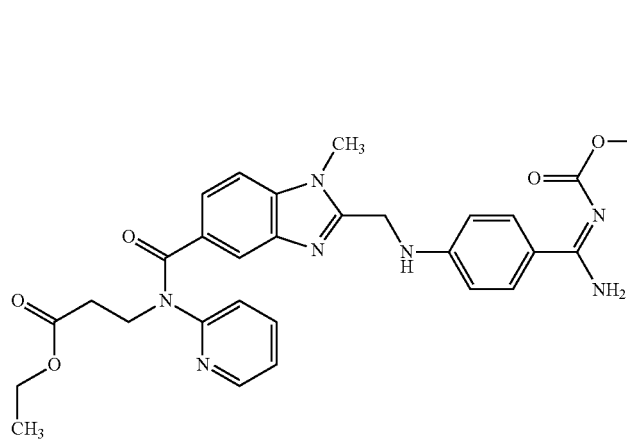
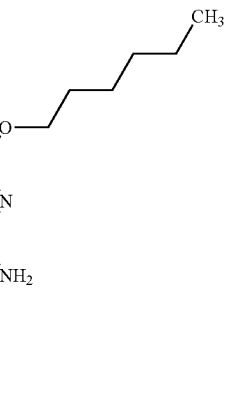

Chemical Formula I

Since dabigatran etexilate is almost insoluble in a medium at pH of >4.0, an acidic environment benefits the dissolution of the main active ingredient dabigatran etexilate from a pharmaceutical preparation and in vivo absorption thereof. Patent Publication No. CN101632668 A discloses that pharmaceutically acceptable organic acids, such as tartaric acid, fumaric acid, succinic acid, citric acid, malic acid, glutamic acid or aspartic acid, can be used as solubilization and dissolution promoters of dabigatran etexilate. This patent application also discloses that the drug layer and the acid-containing core material need to use a separation layer composed of a water-soluble polymer to separate therebetween. The preparation needs that the water solubility of the selected acid should be at least greater than 1 g/250 ml water.

CN102793699 A discloses a composition comprising vitamin C and dabigatran etexilate, and vitamin C is safer to the human body compared to other organic acids, thus the use of vitamin C will improve the safety of the composition. However, since the metabolic process of vitamin C in the body is very complicated, the dissolution of dabigatran etexilate cannot achieve the desired effects either by simply mixing vitamin C and dabigatran etexilate or by physically separating them. The applicant has surprisingly found that the above technical problems can be solved by way of separation with a semipermeable film, and the desired effects can be achieved.

SUMMARY OF THE INVENTION

As the first aspect of the present invention, the present invention provides a pharmaceutical composition of dabigatran etexilate suitable for oral administration, characterized in that the composition comprises a vitamin C layer and a dabigatran etexilate layer, and the vitamin C layer and the dabigatran etexilate layer are separated by a semipermeable film layer.

As the second aspect of the present invention, the present invention also provides a method for preparing the pharmaceutical composition of dabigatran etexilate suitable for oral administration, which comprises:

(1) taking and placing granular vitamin C into a fluidized bed, fluidizing and layering a suspension comprising powdered vitamin C, water and an optional binder and/or filler, and sieving granules having a particle size of between 0.6 mm and 0.8 mm as vitamin C cores;

(2) placing the vitamin C cores into the fluidized bed, and fluidizing and layering a suspension comprising a water-soluble polymer, water and an optional dispersant and/or plasticizer, to give granule 1 having a water-soluble polymer layer;

(3) placing the granule 1 into the fluidized bed, fluidizing and layering a suspension comprising a water-soluble compound, a water-insoluble compound, an alcohol or alcohol solution, and an optional anti-sticking agent and/or plasticizer, and sieving granules of 1 mm or less as granule 2 having a semipermeable film layer;

(4) placing the granule 2 into the fluidized bed, fluidizing and layering a suspension comprising dabigatran etexilate or pharmaceutically acceptable salts thereof, an alcohol and an optional binder and/or dispersant, and sieving granules of 1.5 mm or less as granule 3 having a dabigatran etexilate layer; and (5) optionally, coating the granule 3 with a coating layer.

As the third aspect of the present invention, the present invention also provides a solid preparation comprising the above-mentioned pharmaceutical composition of dabigatran etexilate.

As the fourth aspect of the present invention, the present invention also relates to a use of the pharmaceutical composition of the present invention in preparing a medicament for treatment of thromboembolic diseases.

BRIEF DESCRIPTION OF THE DRAWING

The FIGURE is a cross-sectional schematic view of the dabigatran etexilate granule as one of the preferred embodiments of the present invention.

DETAILED EMBODIMENTS OF THE INVENTION

As the first aspect of the present invention, the present invention provides a pharmaceutical composition of dabigatran etexilate suitable for oral administration, characterized in that the composition comprises a vitamin C layer and a dabigatran etexilate layer, and the vitamin C layer and the dabigatran etexilate layer are separated by a semipermeable film layer.

The semipermeable film layer according to the present invention can be hydrated in a dissolution solution to generate pores, which allow the dissolution solution to penetrate into the acidic cores. The acidic cores are dissolved and slowly released through the pores to produce an acidic microenvironment, thereby promoting the dissolution of the outer drug. Also, the semipermeable film layer can enclose the acidic cores during the dissolution, so as to prevent the separation of the cores from the outer drug layer.

The semipermeable film layer of the present invention preferably comprises a water-soluble compound and a water-insoluble compound. Among them, the water-soluble compound and the water-insoluble compound are dissolved by an alcohol or alcoholic solution, which preferably is isopropanol, anhydrous ethanol or ethanol solution.

The water-soluble compound is selected from methylcellulose, hydroxypropylcellulose, hydroxypropylm ethylcellulose, povidone, sodium carboxymethylcellulose, hydroxypropylmethylcellulose phthalate, pectin, cyclodextrin, galactomannan, polyethylene glycol with an average molecular weight of 4000 or more, gelatin, water-soluble monosaccharide or polysaccharide, or a mixture of two or more thereof; preferably lactose, sucrose, methylcellulose, hydroxypropylcellulose, hydroxypropylmethylcellulose, PEG-6000, povidone or sodium carboxymethylcellulose; more preferably hydroxypropylcellulose or povidone.

The water-insoluble compound is selected from ethylcellulose, HPMCAS, HPMCP, methacrylic acid copolymer, or a mixture of two or more thereof, wherein the methacrylic acid copolymer includes, but not limited to, EUDRAGRIT® E, EUDRAGRIT® R, EUDRAGRIT® S, EUDRAGRIT® L, EUDRAGRIT® RS or EUDRAGRIT® LD; preferably ethylcellulose, HPMCAS, EUDRAGRIT® S100, EUDRAGRIT® L100 or HPMCP; more preferably ethylcellulose.

A mass ratio of the water-soluble compound to the water-insoluble compound in the semipermeable film layer is 1:0.1 to 1:10, preferably 1:0.2 to 1:5, more preferably 1:0.5 to 1:1.

The semipermeable film layer can further comprise an anti-sticking agent and/or a plasticizer. The anti-sticking agent can be selected from talc powder, magnesium stearate, stearic acid, hydrogenated vegetable oil, glyceryl behenate, or a mixture of two or more thereof; preferably talc powder. The plasticizer can be selected from triethyl citrate, tributyl citrate, glycerol triacetate, polyethylene glycol or a mixture of two or more thereof; preferably polyethylene glycol.

The vitamin C layer can only comprise vitamin C, and can further comprise a binder and/or filler. The vitamin C can be granular vitamin C, powdered vitamin C, or a combination of both. The binder can be selected from hydroxypropylcellulose, hydroxypropylmethylcellulose, povidone, sodium carboxym ethylcellulose, methylcellulose, pectin, arabic gum or a mixture of two or more thereof; preferably hydroxypropylcellulose, hydroxypropylmethylcellulose, povidone or arabic gum; more preferably hydroxypropylcellulose or arabic gum. The filler can be selected from microcrystalline cellulose, lactose, starch, mannitol, pregelatinized starch, dextrin or a mixture of two or more thereof; preferably microcrystalline cellulose.

The dabigatran etexilate layer can only comprise dabigatran etexilate, and can further comprise a binder and/or dispersant. The binder can be selected from hydroxypropylcellulose, hydroxypropylm ethylcellulose, m ethylcellulose, hydroxyethylcellulose, sodium carboxymethylcellulose, povidone, N-vinylpyrrolidone, arabic gum, or a mixture of two or more thereof; preferably hydroxypropylcellulose, hydroxypropylmethylcellulose, sodium carboxymethylcellulose, povidone or arabic gum; more preferably hydroxypropylcellulose or sodium carboxymethylcellulose. The binder is preferably dissolved by alcohol, preferably isopropanol. The above-mentioned dispersant can be an anti-sticking agent, such as talc powder, magnesium stearate, stearic acid, hydrogenated vegetable oil, glyceryl behenate, or a mixture of two or more thereof; preferably talc powder.

The above-mentioned semipermeable film layer has a weight gain of 0.5 wt % to 20 wt %, preferably 2 wt % to 10 wt %, more preferably 5 wt % to 10 wt % with respect to the vitamin C layer.

The weight ratio of the above-mentioned dabigatran etexilate layer to the vitamin C layer is from 1:0.15 to 1:1.8, preferably from 1:0.6 to 1:1.

In certain specific embodiments, in addition to the above-mentioned semipermeable film layer, a water-soluble polymer layer can be further comprised between the vitamin C layer and the dabigatran etexilate layer. The water-soluble polymer can be selected from hydroxypropylcellulose, hydroxypropylmethylcellulose, povidone, sodium carboxymethylcellulose, methylcellulose, pectin, arabic gum or a mixture of two or more thereof; preferably hydroxypropylcellulose, sodium carboxymethylcellulose, povidone or arabic gum; more preferably hydroxypropylcellulose or arabic gum. In certain specific embodiments, the water-soluble polymer is arabic gum.

The above-mentioned water-soluble polymer layer can further comprise a dispersant and/or plasticizer. The dispersant can be an anti-sticking agent, such as talc powder, magnesium stearate, stearic acid, hydrogenated vegetable oil, glyceryl behenate or a mixture of two or more thereof, preferably talc powder. The plasticizer can be selected from triethyl citrate, tributyl citrate, glycerol triacetate, polyethylene glycol, or a mixture of two or more thereof; preferably polyethylene glycol.

The weight gain ratio of the water-soluble polymer layer to the semipermeable film layer is from 1:0.1 to 1:10, preferably from 1:0.2 to 1:5, more preferably from 1:1 to 1.1.1.

The pharmaceutical composition of the present invention includes, but not limited to, granules, tablets, pills, and pellets. The granules, tablets, pills or pellets can be multilayer structure. The relative position of the vitamin C layer and the dabigatran etexilate layer is randomly changeable in the multilayer structure. For example, the vitamin C layer is located in the relative inner layer, and the dabigatran etexilate layer, which is separated by a semipermeable film layer, or by a water-soluble polymer layer and a semipermeable film layer, is located in the relative outer layer; alternatively, the dabigatran etexilate layer is located in the relative inner layer, and the vitamin C layer, which is separated by a semipermeable film layer, or by a water-soluble polymer layer and a semipermeable film layer, is located in the relative outer layer. In this case, the vitamin C layer or the dabigatran etexilate layer can be also coated outside of the separation layer (i.e., the semipermeable film layer, or the water-soluble polymer layer and semipermeable film layer) in the form of a coating layer.

A preferred embodiment of the present invention is a multi-granular preparation, wherein each granule is of the structure as shown in the FIG. 1. The vitamin C is contained in the spherical or substantially spherical acidic core of the granule; next, a separation layer composed of a water-soluble polymer layer and a semipermeable film layer is included for separating the vitamin C acidic core and the dabigatran etexilate layer; next, the separation layer is further surrounded by the dabigatran etexilate layer having the same spherical shape; optionally, the dabigatran etexilate layer is further surrounded by a coating layer.

The above-mentioned coating can comprise a film former and/or a plasticizer and/or a pigment commonly used in drugs. The film former can be hydroxypropylcellulose, hydroxypropylm ethylcellulose, povidone, sodium carboxymethylcellulose, methylcellulose, or a mixture of two or more thereof. The plasticizer can be triethyl citrate, tributyl citrate, glycerol triacetate, polyethylene glycol, or a mixture of two or more thereof. The pigment can be titanium dioxide, iron oxide yellow, iron oxide red, or a mixture of two or more thereof.

As the second aspect of the present invention, the present invention also provides a method for preparing the pharmaceutical composition of dabigatran etexilate suitable for oral administration, and the method comprises the following steps:

(1) taking and placing the granular vitamin C into a fluidized bed, fluidizing and layering a suspension comprising powdered vitamin C, water and an optional binder and/or filler, and sieving granules having a particle size of between 0.6 mm and 0.8 mm as vitamin C cores;

(2) placing the vitamin C cores into the fluidized bed, and fluidizing and layering a suspension comprising a water-soluble polymer, water and an optional dispersant and/or plasticizer, to give granule 1 having a water-soluble polymer layer;

(3) placing the granule 1 into the fluidized bed, fluidizing and layering a suspension comprising a water-soluble compound, a water-insoluble compound, an alcohol or alcohol solution, and an optional anti-sticking agent and/or plasticizer, and sieving granules of 1 mm or less as granule 2 having a semipermeable film layer;

(4) placing the granule 2 into the fluidized bed, fluidizing and layering a suspension comprising dabigatran etexilate or pharmaceutically acceptable salts thereof, an alcohol and an optional binder and/or dispersant, and sieving granules of 1.5 mm or less as granule 3 having a dabigatran etexilate layer; and (5) optionally, coating the granule 3 with a coating layer.

As one preferred embodiment, the method comprises the following steps:

taking and placing the granular vitamin C into the fluidized bed, fluidizing and layering a suspension comprising arabic gum, the powdered vitamin C and water, and sieving granules having a particle size of between 0.6 mm and 0.8 mm as the vitamin C cores;

placing the vitamin C cores into the fluidized bed, and fluidizing and layering a suspension comprising arabic gum, talc powder and water, to give granule 1 having a water-soluble polymer layer;

taking hydroxypropylcellulose and ethylcellulose, adding with isopropyl alcohol, stirring and dissolving, followed by adding and fully suspending talc powder by stirring, to give a suspension;

placing the granule 1 into the fluidized bed, fluidizing and layering a suspension comprising hydroxypropylcellulose, ethylcellulose and talc powder, and sieving granule of 1 mm or less as granule 2 further having a semipermeable film layer; and placing the granule 2 into the fluidized bed, fluidizing and layering a suspension comprising hydroxypropylcellulose, talc powder, dabigatran etexilate and isopropanol, and sieving granules of 1.5 mm or less as granule 3 further having a dabigatran etexilate layer.

The method for preparing the above-mentioned granular vitamin C includes, but not limited to, a fluidized bed, a coating tank or a device for extrusion-spheronization.

The above-mentioned granule 3 can be further coated with a coating layer, and the coating method for a coating layer includes, but not limited to, a fluidized bed, a coating tank or commonly used equipment for coating a film.

As the third aspect of the present invention, the present invention also provides a solid preparation comprising the above-mentioned pharmaceutical composition of dabigatran etexilate. The form of the solid preparation can be granules, tablets or capsules. In certain specific embodiments, the solid preparation is in the form of capsules.

As the fourth aspect of the present invention, the present invention also relates to the use of the pharmaceutical composition according to the present invention for preparing a medicament for treating thromboembolic diseases.

In the present invention, unless specifically indicated, dabigatran etexilate refers to the dabigatran etexilate represented by Formula I and the pharmaceutically acceptable salts thereof. The pharmaceutically acceptable salts include, but not limited to, dabigatran etexilate mesylate.

In the present invention, the fluidization and layering refers to a method of coating a suspension onto a surface of a solid granule using a fluidized bed.

In the present invention, HPMCP refers to hydroxypropylmethylcellulose phthalate.

In the present invention, HPMCAS refers to hydroxypropylmethylcellulose acetate succinate.

In the present invention, unless specifically indicated, the semipermeable film layer refers to a coating layer having certain strength and capable of generating pores in dissolution mediums.

In a large number of in-depth studies on the vitamin C layer, the separation layer and the dabigatran etexilate layer, the present inventor found that the use of a semipermeable layer for separating the vitamin C layer and the dabigatran etexilate layer can provide a well acidic microenvironment for the dissolution of dabigatran etexilate, thereby significantly improving the in vitro dissolution of dabigatran etexilate.

EXAMPLES

Hereinafter, the technical solutions of the present invention will be illustrated by specific Examples, but the protection scope of the present invention is not limited to the scope of the Examples. The reagents used are commercially available. In the Examples, unless specifically stated, "%" means percentage by weight.

Comparative Example 1

Formulation:

| Ingredients | Weight of the ingredients (g) | | | |
|---|---|---|---|---|
| | Vitamin C layer | Water-soluble polymer layer | Dabigatran etexilate layer | Total weight (g) |
| Powdered vitamin C | 62.39 | — | — | 62.39 |
| Granular vitamin C | 40.78 | — | — | 40.78 |
| Arabic gum | 5.57$^a$ | 4.47$^b$ | — | 10.04 |
| Talc powder | — | 8.93$^a$ | 19.02$^b$ | 27.95 |
| Hydroxypropylcellulose | — | — | 19.02 | 19.02 |
| Dabigatran etexilate mesylate | — | — | 126.83 | 126.83 |

Preparation Method:

1.1) The formulated amount of arabic gum$^a$ was taken, added with 57 ml of water and dissolved by stirring, and then the formulated amount of the powdered vitamin C was added and fully suspended by stirring, to give a suspension;

1.2) the formulated amount of the granular vitamin C was taken and placed into a fluidized bed, and the suspension prepared in step 1.1) was fluidized and layered thereon; processing parameters: the atomization pressure is 1500 mbar to 1700 mbar, the temperature of inlet air is between 60° C. and 70° C., and the materials are maintained at a temperature of between 40° C. and 50° C.;

1.3) after the layering was finished, the granules having a particle size of between 0.6 mm and 0.8 mm were sieved as the vitamin C cores, wherein the moisture should be ≤0.7%;

2.1) the formulated amount of arabic gum$^b$ was taken, added with water and dissolved by stirring, and then the formulated amount of talc powder$^a$ was added and fully suspended by stirring, to give a suspension;

2.2) the formulated amount of the vitamin C cores prepared in step 1.3) (the sum of the formulated amounts of the powdered vitamin C, the granular vitamin C and arabic gum$^a$ in the vitamin C core materials) were taken and placed into the fluidized bed, and the suspension prepared in step 2.1) was fluidized and layered thereon; processing parameters: the atomization pressure is 1300 mbar to 1500 mbar, the temperature of inlet air is between 50° C. and 60° C., the materials are maintained at a temperature of between 35° C. and 45° C.; and granule 1 having a water-soluble polymer layer was prepared;

3.1) the formulated amount of hydroxypropylcellulose was taken, added with isopropyl alcohol and dissolved by stirring, then the formulated amount of talc powder$^b$ was added and fully suspended by stirring, and the resulting suspension was cooled down to a temperature below 5° C.;

3.2) the formulated amount of dabigatran etexilate mesylate was taken, added into the suspension prepared in step 3.1) under stirring, and uniformly dispersed with stirring;

3.3) the granule 1 prepared in the above-mentioned step 2.2) was taken and placed into the fluidized bed, and the suspension prepared in step 3.2) was fluidized and layered; processing parameters: the atomization pressure is 1800 mbar to 2200 mbar, the temperature of inlet air is between 35° C. and 55° C., and the materials are maintained at a temperature of between 28° C. and 40° C.; the weight loss during drying of the granules should be 0.7%;

3.4) after the layering was finished, the granules of 1.5 mm or less were sieved.

Comparative Example 2

Formulation:

| Ingredients | Weight of the ingredients (g) | | | | |
|---|---|---|---|---|---|
| | Vitamin C layer | Water-soluble polymer layer 1 | Water-soluble polymer layer 2 | Dabigatran etexilate layer | Total weight (g) |
| Powdered vitamin C | 62.39 | — | — | — | 62.39 |
| Granular vitamin C | 40.78 | — | — | — | 40.78 |
| Arabic gum | 5.57$^a$ | 2.90$^b$ | — | — | 8.47 |
| Talc powder | — | 5.80$^a$ | 4.70$^b$ | 19.02$^c$ | 29.52 |
| Hydroxypropylcellulose | — | — | 4.70$^a$ | 19.02$^b$ | 23.72 |
| Dabigatran etexilate mesylate | — | — | — | 126.83 | 126.83 |

Preparation Method:

By reference to the preparation method of Comparative Example 1, the vitamin C cores were firstly prepared with the powdered vitamin C, the granular vitamin C and arabic gum$^a$, the suspension comprising arabic gum$^b$ and talc powder$^a$ was fluidized and layered thereon, then the suspension comprising hydroxypropylcellulose$^a$ and talc powder$^b$ was fluidized and layered, and finally the suspension comprising dabigatran etexilate, hydroxypropylcellulose$^b$ and talc powder$^c$ was fluidized and layered and the prepared granules were sieved.

Comparative Example 3

Preparation of Dabigatran Etexilate Capsules 287.01 mg of the pellets in Comparative Example 1 were taken and filled into hollow plant capsules of No. 1, to give the dabigatran etexilate mesylate capsules with 110 mg strength (calculated by $C_{34}H_{41}N_7O_5$).

Comparative Example 4

Preparation of Dabigatran Etexilate Capsules 195.68 mg of the pellets in Comparative Example 1 were taken and filled into hollow plant capsules of No. 2, to give the dabigatran etexilate mesylate capsules with 75 mg strength (calculated by $C_{34}H_{41}N_7O_5$).

Comparative Example 5

Preparation of Dabigatran Etexilate Capsules 291.71 mg of the pellets in Comparative Example 1 were taken and filled into hollow plant capsules of No. 1, to give the dabigatran etexilate mesylate capsules with 110 mg strength (calculated by $C_{34}H_{41}N_7O_5$).

Example 1

Formulation:

|  | Weight of the ingredients (g) | | | | |
|---|---|---|---|---|---|
| Ingredients | Vitamin C layer | Water-soluble polymer layer | Semi-permeable film layer | Dabigatran etexilate layer | Total weight (g) |
| Powdered vitamin C | 62.39 | — | — | — | 62.39 |
| Granular vitamin C | 40.78 | — | — | — | 40.78 |
| Arabic gum | $5.57^a$ | $2.90^b$ | — | — | 8.47 |
| Talc powder | — | $5.80^a$ | $4.70^b$ | $19.02^c$ | 29.52 |
| Ethylcellulose | — | — | 1.56 | — | 1.56 |
| Hydroxy-propylcellulose | — | — | $3.14^a$ | $19.02^b$ | 22.16 |
| Dabigatran etexilate mesylate | — | — | — | 126.83 | 126.83 |

Preparation Method:

1.1) the formulated amount of arabic gum$^a$ was taken, added with 57 ml of water and dissolved by stirring, and then the formulated amount of the powdered vitamin C was added and fully suspended by stirring, to give a suspension;

1.2) the formulated amount of the granular vitamin C was taken and placed into a fluidized bed, and then the suspension prepared in step 1.1) was fluidized and layered thereon; processing parameters: the atomization pressure is 1500 mbar to 1700 mbar, the temperature of inlet air is between 60° C. and 70° C., the materials are maintained at a temperature of between 40° C. and 50° C.;

1.3) after the layering was finished, the granules having a particle size of between 0.6 mm and 0.8 mm were sieved out as the vitamin C cores, wherein the moisture should be ≤0.7%;

2.1) the formulated amount of arabic gum$^b$ was taken, added with water and dissolved by stirring, and the formulated amount of talc powder$^a$ was added and fully suspended by stirring, to give a suspension;

2.2) the formulated amount of the vitamin C cores prepared in step 1.3) (the sum of the formulated amounts of the powdered vitamin C, the granular vitamin C and arabic gum$^a$ in the vitamin C core materials) was taken and placed into the fluidized bed, and the suspension prepared in step 2.1) was fluidized and layered thereon; processing parameters: the atomization pressure is 1300 mbar to 1500 mbar, the temperature of inlet air is between 50° C. and 60° C., the materials are maintained at a temperature of between 35° C. and 45° C., and the granule 1 having a water-soluble polymer layer was obtained;

3.1) the formulated amounts of hydroxypropylcellulose$^a$ and ethylcellulose, were taken, added with isopropyl alcohol and dissolved by stirring, and then the formulated amount of talc powder$^b$ was added and fully suspended by stirring, to give a suspension;

3.2) the granule 1 prepared in step 2.2) was taken and placed into the fluidized bed, and the suspension prepared in step 3.1) was fluidized and layered thereon; processing parameters: the atomization pressure is 1800 mbar to 2000 mbar, the temperature of inlet air is between 50° C. and 60° C., and the materials are maintained at a temperature of between 35° C. and 50° C.;

3.3) after the layering was finished, the granules of 1 mm or less were sieved as granule 2 having a semipermeable film layer;

4.1) the formulated amount of hydroxypropylcellulose$^b$ was taken, added with isopropyl alcohol and dissolved by stirring, then the formulated amount of talc powder$^c$ was added and fully suspended with stirring, and the resulting suspension was cooled down to a temperature below 5° C.;

4.2) the formulated amount of dabigatran etexilate mesylate was taken, added into the suspension prepared in step 4.1) under stirring, and uniformly dispersed by stirring;

4.3) the granule 2 prepared in step 3.3) was taken and added into the fluidized bed, and the suspension prepared in step 4.2) was fluidized and layered thereon; processing parameters: the atomization pressure is 1800 mbar to 2200 mbar, the temperature of inlet air is between 35° C. and 55° C., and the materials are maintained at a temperature of between 28° C. and 40° C.; and the weight loss during drying of the granules should be ≤0.7%;

4.4) after the layering was finished, the granules of 1.5 mm or less were sieved. The formulation granules of Examples 2 to 7 were prepared with reference to the preparation method of Example 1.

Example 2

Formulation:

|  | Weight of the ingredients (g) | | | | |
|---|---|---|---|---|---|
| Ingredients | Vitamin C layer | Water-soluble polymer layer | Semi-permeable film layer | Dabigatran etexilate layer | Total weight (g) |
| Powdered vitamin C | 62.39 | — | — | — | 62.39 |
| Granular vitamin C | 40.78 | — | — | — | 40.78 |
| Hydroxypropyl-methylcellulose | $5.57^a$ | $0.72^b$ | — | $19.02^c$ | 25.31 |
| Talc powder | — | $1.44^a$ | — | $19.02^b$ | 20.46 |
| Lactose | — | — | 19.8 | — | 19.8 |
| HPMCAS | — | — | 1.98 | — | 1.98 |
| Dabigatran etexilate mesylate | — | — | — | 126.83 | 126.83 |

Preparation Method:

By reference to the preparation method of Example 1, the vitamin C cores were firstly prepared with the powdered Vitamin C, the granular vitamin C and hydroxypropylmethylcellulose$^a$; then the suspension comprising hydroxypropylmethylcellulose$^b$ and talc powder$^b$ (wherein the dispersion medium is water) was fluidized and layered, to give the granule having a water-soluble polymer layer; then the coating solution comprising lactose and HPMCAS (wherein the dispersion medium is a 80% ethanol solution) was fluidized and layered, to give the granule having a semipermeable film layer; and finally the suspension comprising dabigatran etexilate, hydroxypropylmethylcellulose[c] and talc powder[b] was fluidized and layered, and the granules having a dabigatran etexilate layer were obtained by sieving.

Example 3

Formulation:

| Ingredients | Weight of the ingredients (g) | | | | |
|---|---|---|---|---|---|
| | Vitamin C layer | Water-soluble polymer layer | Semi-permeable film layer | Dabigatran etexilate layer | Total weight (g) |
| Granular vitamin C | 108.7 | — | — | — | 108.7 |
| Povidone (K30) | — | 5.4[a] | — | 25.37[b] | 30.77 |
| Talc powder | — | 5.4[a] | — | 25.37[b] | 30.77 |
| Sucrose | — | — | 9.0 | — | 9.0 |
| Eugragit S100 | — | — | 1.8 | — | 1.8 |
| Dabigatran etexilate mesylate | — | — | — | 126.83 | 126.83 |

Preparation Method:

By reference to the preparation method of Example 1, the granular vitamin C having a particle size of 0.6 mm to 0.8 mm were sieved out as the vitamin C cores; then the suspension comprising povidone (K30)[a] and talc powder[a] (wherein the dispersion medium is water) was fluidized and layered, to give the granules having a water-soluble polymer layer; subsequently, the suspension comprising sucrose (d50≤5 μm, d90≤15 μm) and Eugragit S100 (wherein the dispersion medium is an anhydrous ethanol) was fluidized and layered, to give the granules having a semipermeable film layer; and finally the suspension comprising dabigatran etexilate, povidone (K30)[b] and talc powder[b] was fluidized and layered, and the granule having a dabigatran etexilate layer were obtained by sieving.

Example 4

Formulation:

| Ingredients | Weight of the ingredients (g) | | | | |
|---|---|---|---|---|---|
| | Vitamin C layer | Water-soluble polymer layer | Semi-permeable film layer | Dabigatran etexilate layer | Total weight (g) |
| Granular vitamin C | 25.37 | — | — | — | 25.37 |
| Sodium carboxy-methylcellulose | — | 1.68[a] | — | 25.37[b] | 27.05 |
| Talc powder | — | 0.84[a] | — | 12.68[b] | 13.52 |
| Hydroxy-propylcellulose | — | — | 1.68 | — | 1.68 |
| Eugragit L100 | — | — | 0.84 | — | 0.84 |
| Dabigatran etexilate mesylate | — | — | — | 126.83 | 126.83 |

Preparation Method:

By reference to the preparation method of Example 1, the granular vitamin C having a particle size of 0.6 mm to 0.8 mm were sieved out as the vitamin C cores; then the suspension comprising sodium carboxymethylcellulose[a] and talc powder[a] (wherein the dispersion medium is water) was fluidized and layered, to give the granule having a water-soluble polymer layer; subsequently, the suspension comprising hydroxypropylcellulose and Eugragit L100 (wherein the dispersion medium is an anhydrous ethanol) was fluidized and layered, to give the granule having a semipermeable film layer; and finally the suspension comprising dabigatran etexilate, sodium carboxymethylcellulose[b] and talc powder[b] was fluidized and layered, and the granules having a dabigatran etexilate layer were obtained by sieving.

Example 5

Formulation:

| Ingredients | Weight of the ingredients (g) | | | | |
|---|---|---|---|---|---|
| | Vitamin C layer | Water-soluble polymer layer | Semi-permeable film layer | Dabigatran etexilate layer | Total weight (g) |
| Powdered vitamin C | 169.10 | | | | 169.10 |
| Granular vitamin C | 84.55 | — | — | — | 84.55 |
| Arabic gum | 16.91[a] | — | — | 12.68[b] | 29.59 |
| Talc powder | — | 1.35[a] | — | 25.37[b] | 26.72 |
| Methylcellulose | — | 1.35[a] | 6.76[b] | — | 8.11 |
| Hydroxypropyl-methylcellulose phthalate (HPMCP) | — | — | 6.76 | — | 6.76 |
| Dabigatran etexilate mesylate | — | — | — | 126.83 | 126.83 |

Preparation Method:

By reference to the preparation method of Example 1, the vitamin C cores were firstly prepared with the powdered vitamin C, the granular vitamin C and arabic gum[a]; then the suspension comprising methylcellulose[a] and talc powder[a] (wherein the dispersion medium is water) was fluidized and layered, to obtain particles having a water-soluble polymer layer; subsequently, the coating solution comprising methylcellulose[b] and hydroxypropylmethylcellulose phthalate (HPMCP) (wherein the dispersion medium is a 80% ethanol solution) was fluidized and layered, to give the granules having a semipermeable film layer; and finally a suspension comprising dabigatran etexilate, arabic gum[b] and talcum powder[b] was fluidized and layered, and the granules having a dabigatran etexilate layer were obtained by sieving.

Example 6

Formulation:

| Ingredients | Weight of the ingredients (g) | | | | |
|---|---|---|---|---|---|
| | Vitamin C layer | Water-soluble polymer layer | Semi-permeable film layer | Dabigatran etexilate layer | Total weight (g) |
| Granular vitamin C | 190.25 | — | — | — | 190.25 |
| Talc powder | — | 8.5[a] | — | 25.37[b] | 33.87 |
| Sodium carboxy-methylcellulose | — | 9.5[a] | — | 19.02[b] | 28.52 |
| Polyethylene glycol-6000 | — | 1.0[a] | 0.63[b] | — | 1.63 |
| Ethylcellulose | — | — | 3.15 | — | 3.15 |

-continued

| Ingredients | Weight of the ingredients (g) | | | | |
|---|---|---|---|---|---|
| | Vitamin C layer | Water-soluble polymer layer | Semi-permeable film layer | Dabigatran etexilate layer | Total weight (g) |
| Dabigatran etexilate mesylate | — | — | — | 126.83 | 126.83 |

Preparation Method:

By reference to the preparation method of Example 1, the granular vitamin C having a particle size of 0.6 mm to 0.8 mm were sieved out as the vitamin C cores; then the suspension comprising sodium carboxymethylcellulose$^a$, talc powder$^a$ and polyethylene glycol-6000$^a$ (wherein the dispersion medium is water) was fluidized and layered, to give the granule having a water-soluble polymer layer; subsequently, the suspension comprising polyethylene glycol-6000$^b$ and ethylcellulose (wherein the dispersion medium is an anhydrous ethanol) was fluidized and layered, to give the granule having a semipermeable film layer; and finally the suspension comprising dabigatran etexilate, sodium carboxymethylcellulose$^b$ and talc powder$^b$, was fluidized and layered, and the granule having a dabigatran etexilate layer was obtained by sieving.

Example 7

Formulation:

| Ingredients | Weight of the ingredients (g) | | | | |
|---|---|---|---|---|---|
| | Vitamin C layer | Water-soluble polymer layer | Semi-permeable film layer | Dabigatran etexilate layer | Total weight (g) |
| Powdered vitamin C | 169.10 | — | — | — | 169.10 |
| Granular vitamin C | 84.55 | — | — | — | 84.55 |
| Arabic gum | 13.53 | — | — | — | 13.53 |
| Talc powder | — | 1.30$^a$ | — | 12.68$^b$ | 13.98 |
| Sodium carboxymethylcellulose | — | 13.00$^a$ | 0.13$^b$ | 12.68$^c$ | 25.81 |
| Ethylcellulose | — | — | 1.30 | — | 1.30 |
| Dabigatran etexilate mesylate | — | — | — | 126.83 | 126.83 |

Preparation Method:

By reference to the preparation method of Example 1, the vitamin C cores were firstly prepared with the powdered vitamin C, the granular vitamin C and arabic gum; then the suspension comprising sodium carboxymethylcellulose$^a$ and talc powder$^a$ (wherein the dispersion medium is water) was fluidized and layered, to give the granule having a water-soluble polymer layer; subsequently, the coating solution comprising sodium carboxymethylcellulose$^b$ and ethylcellulose (wherein the dispersion medium is an anhydrous ethanol) was fluidized and layered, to give the granule having a semipermeable film layer; and finally the suspension comprising dabigatran etexilate, sodium carboxymethylcellulose$^c$ and talc powder$^b$ was fluidized and layered, and the granule having a dabigatran etexilate layer was obtained by sieving.

Example 8

Preparation of Dabigatran Etexilate Capsules 291.71 mg of the pellets in Example 2 were taken and filled into hollow plant capsules of No. 1, to give the dabigatran etexilate mesylate capsules with 110 mg strength (calculated by $C_{34}H_{41}N_7O_5$).

Example 9

Preparation of Dabigatran Etexilate Capsules 198.88 mg of the pellets in Example 2 were taken and filled into hollow plant capsules of No. 2, to give the dabigatran etexilate mesylate capsules with 75 mg strength (calculated by $C_{34}H_{41}N_7O_5$).

Example 10

Comparison of the In Vitro Dissolution Characteristics of Dabigatran Etexilate Capsules The preparations in Comparative Examples 3 to 5 and Examples 8 to 9 and the commercially available reference preparation were taken respectively. According to the method for determining dissolution rate (the first method in the Appendix X C of the second part of Chinese Pharmacopeia 2010), 900 ml of a dissolution medium was added, the rotating speed is 100 revolutions per minute, and the operation was carried out according to this method. The dissolution rates were measured by sampling at 10, 20, 30, 45 and 60 minutes respectively.

The results are shown in Tables 1 and 2:

TABLE 1

Comparison of the dissolution characteristics (strength: 110 mg (calculated by $C_{34}H_{41}N_7O_5$))

| Accumulative amount of dissolution | Water | | | | buffer of pH 4.0 | | | |
|---|---|---|---|---|---|---|---|---|
| | Comparative Example 3 | Comparative Example 5 | Example 8 | Pradaxa ® reference preparation | Comparative Example 3 | Comparative Example 5 | Example 8 | Pradaxa ® reference preparation |
| 10 min | 6.8 | 7.2 | 7.1 | 4.0 | 2.0 | 1.7 | 5.7 | 2.0 |
| 20 min | 67.4 | 68.5 | 68.9 | 69.8 | 30.1 | 27.5 | 31.4 | 29.9 |
| 30 min | 80.3 | 79.6 | 86.6 | 88.0 | 54.4 | 56.4 | 56.6 | 54.9 |
| 45 min | 83.2 | 82.1 | 94.0 | 93.6 | 70.8 | 71.6 | 77.3 | 78.2 |
| 60 min | 85.4 | 83.9 | 96.5 | 96.4 | 79.4 | 80.8 | 86.3 | 87.8 |

TABLE 2

Comparison of the dissolution characteristics (strength: 75 mg (calculated by $C_{34}H_{41}N_7O_5$))

| Accumulative amount of dissolution | Water | | | buffer of pH 4.0 | | |
| --- | --- | --- | --- | --- | --- | --- |
| | Comparative Example 4 | Example 9 | Pradaxa ® reference preparation | Comparative Example 4 | Example 9 | Pradaxa ® reference preparation |
| 10 min | 9.4 | 8.2 | 8.2 | 1.2 | 2.4 | 2.4 |
| 20 min | 81 | 81.5 | 80.1 | 28.1 | 30.3 | 27.8 |
| 30 min | 88 | 92.6 | 92.6 | 56.6 | 58.7 | 54.9 |
| 45 min | 89.6 | 95.2 | 97.5 | 72.7 | 77.0 | 76.8 |
| 60 min | 91.3 | 96.9 | 98.7 | 81.7 | 87.4 | 89.4 |

What is claimed is:

1. A pharmaceutical composition of dabigatran etexilate suitable for oral administration, characterized in that the pharmaceutical composition is a multi-granule preparation in which each granule comprises a spherical or substantially spherical acidic core including Vitamin C, a separation layer comprising a water-soluble polymer layer and a semipermeable film layer, a dabigatran etexilate layer, and an optional coating layer surrounding the dabigatran etexilate layer, wherein the separation layer separates the acidic core including Vitamin C and the dabigatran etexilate layer,
wherein the separation layer is surrounded by the dabigatran etexilate layer having the same spherical shape,
wherein the water-soluble polymer layer is located between the acidic core and the semipermeable film layer,
wherein the semipermeable film layer comprises a water-soluble compound, a water-insoluble compound, and an optional anti-sticking agent and/or plasticizer, the water-soluble compound being lactose, the water-insoluble compound being selected from the group consisting of ethylcellulose and hydroxypropylmethylcellulose acetate succinate (HPMCAS),
wherein the weight ratio of the dabigatran etexilate layer to the acidic core including Vitamin C is 1:0.6 to 1:1.1,
wherein the weight gain ratio of the water-soluble polymer layer to the semipermeable film layer is 1:0.1 to 1:10,
wherein the pharmaceutical composition is in the form of capsules comprising the multi-granule preparation.

2. The pharmaceutical composition according to claim 1, characterized in that the mass ratio of the water-soluble compound to the water-insoluble compound in the semipermeable film layer is 1:0.1 to 1:10.

3. The pharmaceutical composition according to claim 2, characterized in that the semipermeable film layer has a weight gain of 0.5 wt % to 20 wt % with respect to the acidic core including Vitamin C.

4. The pharmaceutical composition according to claim 2, characterized in that the mass ratio of the water-soluble compound to the water-insoluble compound in the semipermeable film layer is 1:0.2 to 1:5.

5. A method for preparing the pharmaceutical composition according to claim 1, characterized in that the method comprises the following steps:

(1) taking and placing granular Vitamin C into a fluidized bed, fluidizing and layering a suspension comprising powdered Vitamin C and water, and sieving granules having a particle size of between 0.6 mm and 0.8 mm as Vitamin C cores;
(2) placing the Vitamin C cores into the fluidized bed, fluidizing and layering a suspension comprising a water-soluble polymer and water, to give granule 1 having a water-soluble polymer layer;
(3) placing the granule 1 into the fluidized bed, fluidizing and layering a suspension comprising a water-soluble compound, a water-insoluble compound, and an alcohol or alcohol solution, and sieving granules of 1 mm or less as granule 2 having a semipermeable film layer;
(4) placing the granule 2 into the fluidized bed, fluidizing and layering a suspension comprising dabigatran etexilate or pharmaceutically acceptable salts thereof, and an alcohol, and sieving granules of 1.5 mm or less as granule 3 having a dabigatran etexilate layer; and
(5) optionally, coating the granule 3 with a coating layer
(6) forming a capsule comprising the optionally coated granule 3.

6. The pharmaceutical composition according to claim 1, characterized in that the weight gain ratio of the water-soluble polymer layer to the semipermeable film layer is 1:0.2 to 1:5.

7. The pharmaceutical composition according to claim 1, wherein the water-insoluble compound is ethylcellulose.

8. The pharmaceutical composition according to claim 1, wherein the water-insoluble compound is HPMCAS.

9. The pharmaceutical composition according to claim 1, wherein the pharmaceutical composition further includes the optional coating layer.

10. The pharmaceutical composition according to claim 1, wherein the semipermeable film layer further includes the optional anti-sticking agent.

11. The pharmaceutical composition according to claim 1, wherein the semipermeable film layer further includes the optional plasticizer.

12. The pharmaceutical composition according to claim 1, wherein the acidic core further includes arabic gum.

13. The pharmaceutical composition according to claim 1, wherein the dabigatran etexilate layer further includes carboxymethylcellulose.

14. The pharmaceutical composition according to claim 13, wherein the acidic core further includes arabic gum.

* * * * *